United States Patent
Cao et al.

(10) Patent No.: US 10,400,268 B2
(45) Date of Patent: Sep. 3, 2019

(54) METHODS AND KITS FOR THE DETECTION OF DNA

(71) Applicant: THE QUEEN'S UNIVERSITY OF BELFAST, Belfast (GB)

(72) Inventors: Cuong Cao, Belfast (GB); Christopher Elliott, Antrim (GB); Claire McVey, Magherafelt (GB)

(73) Assignee: The Queen's University of Belfast, Belfast (GB)

( * ) Notice: Subject to any disclaimer, the term of this patent is extended or adjusted under 35 U.S.C. 154(b) by 34 days.

(21) Appl. No.: 15/341,162

(22) Filed: Nov. 2, 2016

(65) Prior Publication Data
US 2018/0119207 A1    May 3, 2018

(51) Int. Cl.
*C12Q 1/6816*    (2018.01)

(52) U.S. Cl.
CPC .................. *C12Q 1/6816* (2013.01)

(58) Field of Classification Search
CPC .......... C12Q 1/68; C07H 21/04; C12N 15/00; G01N 33/48
See application file for complete search history.

(56) References Cited

U.S. PATENT DOCUMENTS

| | | | |
|---|---|---|---|
| 2002/0155442 A1* | 10/2002 | Mirkin | B82Y 15/00 435/6.11 |
| 2005/0059042 A1 | 3/2005 | Rothberg et al. | |
| 2007/0238096 A1* | 10/2007 | Reich | C07H 21/02 435/5 |
| 2010/0075335 A1 | 3/2010 | Ramos Franca Tavares et al. | |
| 2014/0134609 A1 | 5/2014 | Tan et al. | |

OTHER PUBLICATIONS

Bai et al, Visual detection of sub-femtomole DNA by a gold nanoparticle seeded homogeneous reduction assay: Toward a generalized sensitivity-enhancing strategy, Biosensors and Bioelectronics, 2010, 25, 1984-1988. (Year: 2010).*

(Continued)

*Primary Examiner* — Narayan K Bhat
(74) *Attorney, Agent, or Firm* — Hodgson Russ LLP

(57) ABSTRACT

The present invention is related to methods and kits for the detection of deoxyribonucleic acid (DNA), in particular pathogenic microbial DNA, which provide more simple and sensitive detection of DNA compared to similar methods and kits known in the art. The method comprises a) contacting the sample with a plurality of metal nanoparticles functionalized with one or more ribonucleic acid (RNA) probes; b) forming a heteroduplex between the target DNA and RNA probe on an RNA-functionalized metal nanoparticle; c) contacting the heteroduplex of target DNA and RNA probe on the RNA-functionalized metal nanoparticle with an enzyme that cleaves RNA in a DNA-RNA heteroduplex thereby releasing the target DNA; d) repeating steps (b) and (c) until all, or substantially all, of the RNA probes on the plurality of RNA-functionalized metal nanoparticles have been cleaved from the metal nanoparticles; and e) aggregating the metal nanoparticles from which all, or substantially all, of the RNA probes have been cleaved, thereby indicating the presence of the target DNA.

21 Claims, 7 Drawing Sheets
(7 of 7 Drawing Sheet(s) Filed in Color)
Specification includes a Sequence Listing.

(56) References Cited

OTHER PUBLICATIONS

Kim, et al., Specific and sensitive detection of nucleic acids and RNases using gold nanoparticle-RNA-fluorescent dye conjugates, Chemical Communications, No. 42, pp. 4342-4344 Sep. 19, 2007.
Turkevich, et al., A study of the nucleation and growth processes in the synthesis of colloidal gold, Discussion os the Faraday Society, vol. 11, pp. 55-75 May 18, 1951.
Cui, et al., A universal platform for sensitive and selective calorimetric DNA detection based on EXO III assisted signal amplification, Biosensors and Bioelectronics, vol. 26, No. 5, pp. 2796-2800 Jan. 15, 2011.
Fan, et al., Exonuclease III-based and gold nanoparticle-assisted DNA detection with dual signal amplification, Biosensors and Bioelectronics, vol. 33, No. 1, pp. 211-215 Mar. 15, 2012.
McVey, et al.—Endonuclease controlled aggregation of gold nanoparticles for the ultrasensitive detection of pathogenic bacterial DNA, vol. 92, pp. 502-508 Oct. 27, 2016.
Dougan, et al.—Enhanced oligonucleotide-nanoparticle conjugate stability using thioctic acid modified oligonucleotides, vol. 35, pp. 3668-3675 May 8, 2007.

\* cited by examiner

SEQUENCE LISTING

<160> NUMBER OF SEQ ID NOS: 4

<210> SEQ ID NO 1
<211> LENGTH: 33
<212> TYPE: RNA
<213> ORGANISM: Campylobacter jejuni
<220> FEATURE:
<221> NAME/KEY: misc_feature
<222> LOCATION: (1)..(1)
<223> OTHER INFORMATION: Amino group

<400> SEQUENCE: 1 cccccaggu guggacgacg ucaagucauc aug                     33

<210> SEQ ID NO 2
<211> LENGTH: 27
<212> TYPE: DNA
<213> ORGANISM: Campylobacter jejuni

<400> SEQUENCE: 2
catgatgact tgacgtcgtc cacacct                           27

```
<210> SEQ ID NO 3
<211> LENGTH: 18
<212> TYPE: DNA
<213> ORGANISM: Artificial Sequence
<220> FEATURE:
<223> OTHER INFORMATION: Non-complementary DNA probe 1

<400> SEQUENCE: 3 ccaaccccc agaaagaa                                                          18

<210> SEQ ID NO 4
<211> LENGTH: 45
<212> TYPE: DNA
<213> ORGANISM: Artificial Sequence
<220> FEATURE:
<223> OTHER INFORMATION: Non-complementary probe 2

<400> SEQUENCE: 4
tctattggtg gtaaaactta cgctgcaagt aaagccgaag gtcac                           45
```

METHODS AND KITS FOR THE DETECTION OF DNA

TECHNICAL FIELD

This invention relates to methods and kits for the detection of DNA, in particular pathogenic microbial DNA.

BACKGROUND ART

The on-site and sensitive detection of pathogens is of critical importance to the prevention, surveillance and control of infectious diseases and their outbreak at the first onset. While conventional techniques such as plate culturing, polymerase chain reaction (PCR) and enzyme-linked immunosorbent assay (ELISA) have been used as the predominant detection workhorses, they are limited by either time-consuming procedure, complicated sample pre-treatment, expensive analysis and operation, or inability to be implemented at point-of-testing. Significant efforts have been made to improve the limitations associated with conventional techniques. Among these, gold nanoparticles (AuNPs) have emerged as an excellent candidate for biosensor design owing to their unique properties. For example, colloidal AuNPs exhibit distinct colours and strong absorption bands in the visible range of the electromagnetic spectrum that are not present in the bulk metal. This fascinating optical phenomenon of AuNPs is derived from localized surface plasmon resonance (LSPR), a collective oscillation of free electrons in tandem with the incoming photon frequency. This has provided a range of simplified transducing mechanisms for biosensor design, based on assembly, disassembly, or enlargement of the AuNPs which allow scanometric, colorimetric or even naked-eye determination. Nucleic acid-modified AuNPs have been incorporated into biological sensing platforms to provide improved sensitivity, versatility and portability. Remarkably, the nucleic acid functionalized AuNPs not only provide further functionalities such as specific programmable assembly upon hybridization with their complementary counterparts, but also allow enzymatic cleavage, ligation and extension reactions for biosensor development.

Toward this end, studies have focused on incorporating nuclease enzymes and deoxyribozymes (DNAzyme) to cleave or link oligonucleotides to induce a colorimetric response. DNA endonuclease (DNase $Pb^{2+}$-dependent RNA-cleaving DNAzyme (DNAzyme 8-17), exonuclease III (Exo III) and RNAse H have been used successfully for the detection of $Pb^{2+}$, nucleic acids and folate receptor. DNAzyme 8-17, which cleaves the DNA substrate with a single RNA linkage in the presence of $Pb^{2+}$, has been utilised for the detection of metal ions. In a different approach, incorporating the same 8-17 enzyme, cross-linking of enzyme-substrate and subsequent cleavage and dissociation of AuNPs upon the addition of target analyte ($Pb^{2+}$) has been reported. Several studies have also focused on Exo III enzyme which catalyzes the stepwise removal of mononucleotides from blunt or recessed 3'-hydroxyl terminus of duplex DNA. A universal platform has been developed for the detection of DNA based on Exo III signal amplification. Furthermore, Exo III has been utilized for the colorimetric detection of folate receptor, in which the target induced AuNP aggregation. The utilization of Exo III enzyme has proven highly sensitive due to repeated hybridization and hydrolysis reactions. In a different approach, AuNPs were modified with EcoRI enzyme and a specific, double stranded DNA probe was designed which contained an EcoRI recognition site and complementary sticky ends. AuNP aggregation occurred in the presence of the target (magnesium and phosphate ions), resulting in a colorimetric response. Although highly successful, such enzymatic approaches are limited by the need for restriction binding sites, extensive probe design, and requirement for further amplification steps.

Herein, we present innovative sensing methods and kits based on the unique enzymatic activity of endonucleases, such as RNase H, for the detection of DNA, such as bacterial DNA, at concentrations down to femtomolar level. Due to the ubiquitous nature and high levels found in food, especially poultry, *Campylobacter jejuni* was chosen as the target for assay development and to exemplify the method of the invention (see Examples). The exemplified method utilizes RNA-functionalized AuNPs which form DNA-RNA heteroduplex structures through specific hybridization with target DNA. Once formed, the DNA-RNA heteroduplex is susceptible to RNase H enzymatic cleavage of the RNA probe, allowing DNA to liberate and hybridize with another RNA strand. This continuously happens until all, or substantially all, of the RNA strands are cleaved, leaving the nanoparticles unprotected, or substantially unprotected, and prone to aggregation upon exposure to a high electrolytic medium. The current invention overcomes previous limitations associated with enzyme-based methods in that it does not require further amplification steps. In addition, enzymes such as RNAse H which are not active on single stranded DNA or RNA molecules and only catalyze the cleavage of RNA within a DNA-RNA heteroduplex, do not require specific recognition sites for enzymatic cleavage. Furthermore, there is greater versatility and applicability with regard to probe design and thus potential for multiplexing. RNase H has previously been used for the detection of DNA via RNA cleavage within a DNA-RNA heteroduplex structure and subsequent release of a fluorescence dye to generate a fluorescence signal.[1] That method has a reported limit of detection (LOD) of 10 pM, which highlights the ultra-sensitivity of the method of the present invention which can detect target DNA at 1 pM as determined by the naked eye, or even down to femtomolar level by spectroscopic analysis (see Examples). The fluorescence-based approach mentioned above is further limited by cost due to the synthesis of fluorescein conjugate and requirement for equipment capable of detecting the fluorescence signals. The present invention is significantly different from previous reports as it utilizes the plasmonic properties of metal nanoparticles to produce a colorimetric response, in particular gold nanoparticles which produce a red-to-blue colorimetric response, thus the signal can be visibly detected by the naked eye. In addition, DNA detection can be performed at isothermal conditions in less than three hours. These advantages provide a basis for eradicating the need for a thermal cycler, complicated sample preparation, labelled fluorophores, and expensive and cumbersome read-out equipment. Finally, the application of the present invention to a food matrix has also been assessed and it is evident that the sensitivity and robustness of the assay is conducive for food safety analysis.

SUMMARY OF THE INVENTION

Accordingly, in one aspect, the invention provides a method for detecting a target deoxyribonucleic acid (DNA) in a sample, the method comprising:
  a) contacting the sample with a plurality of metal nanoparticles functionalised with one or more ribonucleic acid (RNA) probes;

b) forming a heteroduplex between the target DNA and RNA probe on an RNA-functionalised metal nanoparticle;

c) contacting the heteroduplex of target DNA and RNA probe on the RNA-functionalised metal nanoparticle with an enzyme that cleaves RNA in a DNA-RNA heteroduplex thereby releasing the target DNA;

d) repeating steps (b) and (c) until all, or substantially all, of the RNA probes on the plurality of RNA-functionalised metal nanoparticles have been cleaved from the metal nanoparticles; and e) aggregating the metal nanoparticles from which all, or substantially all, of the RNA probes have been cleaved, thereby indicating the presence of the target DNA.

Optionally, the metal nanoparticles comprise noble metal nanoparticles. Optionally, the metal nanoparticles consist of noble metal nanoparticles. Optionally, the metal nanoparticles comprise a mixture of different types of noble metal nanoparticles. Alternatively, the metal nanoparticles comprise the same, or substantially the same, type of noble metal nanoparticles, Noble metal nanoparticles show suitable physicochemical properties, such as ease of functionalization and localized surface plasmon resonance, for use in the present invention. As referred to herein, "metals" include alloys of the recited metals. Optionally, the metal nanoparticles are selected from one of more of gold nanoparticles, silver nanoparticles, platinum nanoparticles, copper nanoparticles, palladium nanoparticles, ruthenium nanoparticles, rhodium nanoparticles, osmium nanoparticles, and iridium nanoparticles, or alloys of these metals. Optionally, the metal nanoparticles comprise gold nanoparticles. For the purposes of describing the present invention, metal nanoparticles in the form of gold nanoparticles will be described and will be exemplified in the Examples. However, it will be appreciated that the skilled person may use other metal nanoparticles in place of gold nanoparticles as described herein. It will further be understood that gold nanoparticles are the preferred nanoparticles for use in the present invention since gold nanoparticles can be less toxic, less sensitive to oxidation, and provide more vivid colour and colour changes to allow better naked eye discrimination of aggregation states of the nanoparticles, than other metal nanoparticles.

Optionally, the gold nanoparticles are functionalised with one or more RNA probes by conjugating, optionally covalently conjugating, one or more RNA probes to each metal nanoparticle. Optionally, the metal nanoparticles are functionalised with one or more RNA probes by conjugating, optionally covalently conjugating, one or more RNA probes to each metal nanoparticle via a modification at the 5' end, alternatively at the 3' end, of each RNA probe. A suitable modification is well known to the person skilled in the art and may be, for example, an amine modification, a sulfide modification, a disulfide modification, a thiol modification, or a dithiol modification at the 5' end, alternatively at the 3' end, of each RNA probe. Optionally, the metal nanoparticles are functionalised with one or more RNA probes by conjugating one or more amine-modified RNA probes to each metal nanoparticle. In other words, each of the one or more RNA probes are conjugated to the metal nanoparticles through an amine linkage. Optionally, the metal nanoparticles are functionalised with one or more RNA probes by conjugating one or more sulfide-modified RNA probes to each metal nanoparticle. In other words, each of the one or more RNA probes are conjugated to the metal nanoparticles through a sulfide linkage. Optionally, the metal nanoparticles are functionalised with one or more RNA probes by conjugating one or more disulfide-modified RNA probes to each metal nanoparticle. In other words, each of the one or more RNA probes are conjugated to the metal nanoparticles through a disulfide linkage. Optionally, the metal nanoparticles are functionalised with one or more RNA probes by conjugating one or more thiol-modified RNA probes, optionally an alkanethiol-modified RNA probe, to each metal nanoparticle. In other words, each of the one or more RNA probes are conjugated to the metal nanoparticles through a thiol linkage. Optionally, the metal nanoparticles are functionalised with one or more RNA probes by conjugating one or more dithiol-modified RNA probes to each metal nanoparticle. In other words, each of the one or more RNA probes are conjugated to the metal nanoparticles through a dithiol linkage. Optionally, the metal nanoparticles are functionalised with one or more RNA probes by conjugating one or more dithiol-modified RNA probes to each metal nanoparticle, wherein said one or more dithiol-modified RNA probes are one or more thioctic acid-modified RNA probes. In other words, each of the one or more RNA probes are conjugated to the metal nanoparticles through a thioctic acid linkage. Optionally, the metal nanoparticles are functionalised with one or more RNA probes by conjugating one or more thioctic acid-modified RNA probes to each metal nanoparticle via an N-hydroxysuccimidyl ester of thioctic acid at the 5' end, alternatively at the 3' end, of the RNA probe. Optionally, the metal nanoparticles are functionalised with one or more RNA probes by conjugating one or more thioctic acid-modified RNA probes to each metal nanoparticle via an N-hydroxysuccimidyl (NHS) ester of thioctic acid at the 5' end, alternatively at the 3' end, of the RNA probe. Derivatives of thioctic acid, such as reduced thioctic acid, are also suitable for use in modifying RNA probes as described herein. In addition, other sulphides, disulfides and thiols suitable for use in modifying RNA probes as described herein include sulfides in the form of R—S—R, e.g. 3-(Methylthio)-1-propanol), disulfides in the form of R—S—S—R, e.g. bis(10-carboxydecyl)disulphide), and thiols in the form of R—SH, e.g. alkyl thiols, wherein R represents a unsubstituted or substituted group comprising but not limited to an aliphatic or aromatic alkane, alkene, or other carbon-containing group of atoms including, but not limited to, ethylene glycol derivatives, and thiolated ethylene glycol derivatives such [11-(Methyl-carbonylthio)undecyl]tetra(ethylene glycol), which modifications can coordinate strongly onto the metal surface. Additional thiol modifications include 1-propanethiol, 1-butanethiol, 1-pentanethiol, 1-hexanethiol, 1-heptanethiol, 1-octanethiol, 1-nonanethiol, 1-decanethiol, 1-undecanethiol, 1-dodecanethiol, 1-tetradecanethiol, 1-pentadecanethiol, 1-hexadecanethiol, 1-octadecanethiol, 2-ethylhexanethiol, 2-methyl-1-propanethiol, 3-methyl-1-butanethiol, butyl 3-mercaptopropionate, tert-dodecylmercaptan, and tert-nonylmercaptan. Additional dithiol modifications include 1,2-ethandithiol, 1,3-propanedithiol, 1,4-butanedithiol, 2,3-butanedithiol, 1,5-pentanedithiol, 1,6-hexanedithiol, 1,8-octanedithiol, 1,9-nonanedithiol, tetra(ethylene glycol) dithiol, hexa(ethylene glycol) dithiol, 2,2'-(ethylenedioxy)diethanethiol, and 5,5'-bis(mercaptomethyl)-2,2'-bipyridine. Without wishing to be bound by theory, it is understood that the conjugating, optionally covalently conjugating, one or more RNA probes to each metal nanoparticle via a modification as described herein, in particular, by conjugating one or more thioctic acid-modified RNA probes to each metal nanoparticle via an N-hydroxysuccimidyl (NHS) ester of thioctic acid at the 5' end of the RNA probe, provides more stable RNA-functionalised metal nanoparticles. As used herein, "stable" means that a majority of the RNA probes remain attached to the metal nanoparticles, and the RNA probes are able to hybridize with a DNA target under suitable conditions for detecting nucleic acids, when stored for up to four weeks at 4° C. in a suitable buffer, such as TE buffer. TE buffer typically comprises 10 mM Tris, brought to pH 8.0 with HCl, and 1 mM EDTA.

Optionally, the DNA in the sample is single-stranded DNA. Optionally, the sample contains double-stranded DNA and the sample is treated, prior to or at the same time as step (a) of the method of described herein, such that at least some, all, or substantially all, of the double-stranded DNA dissociates to single-stranded DNA. It is known in the art how one may treat a sample containing double-stranded DNA so that at least some, all, or substantially all, of the double-stranded DNA dissociates to single-stranded DNA. Optionally, the sample may be heated to a suitable temperature such that the double-stranded DNA dissociates to single-stranded DNA. Optionally, the sample may be heated to a suitable temperature for a suitable period of time, such that the double-stranded DNA dissociates to single-stranded DNA. Optionally, the sample may be heated to a suitable temperature wherein the suitable temperature is ≥80° C., optionally ≥85° C., further optionally ≥90° C. Optionally, the sample may be heated to a suitable temperature for at least about 30 seconds, optionally at least about 1 minute, further optionally at least about 2 minutes, to dissociate the double-stranded DNA to single-stranded DNA. Optionally, after the sample has been heated to a suitable temperature, optionally for a suitable period of time, such that the double-stranded DNA dissociates to single-stranded DNA, the sample is maintained at less than about 10° C., optionally at less than about 7.5° C., at less than about 5° C., further at less than about 4° C., in order to prevent the single-stranded DNA re-hybridising to double-stranded DNA. Optionally, the sample is maintained at less than about 10° C., optionally at less than about 7.5° C., at less than about 5° C., further at less than about 4° C., immediately after heating the sample to a suitable temperature, optionally for a suitable period of time, to dissociate the double-stranded DNA to single-stranded DNA. Optionally, the RNA probe on the RNA-functionalised metal nanoparticle is single-stranded DNA.

Optionally, the RNA probe is of sufficient length to allow the probe to hybridise with the DNA target. The RNA probes useful in the methods and kits disclosed herein may be of varying lengths. Optionally, the RNA probe is about 5 to about 200, optionally about 5 to about 100, optionally about 5 to about 75, optionally about 10 to about 50, further optionally about 17 to about 40, nucleotides in length. Optionally, the RNA probe, as disclosed herein, comprises a complementarity domain, which domain comprises part of, or the whole, of the nucleotide sequence of the RNA probe. Optionally, the nucleotide sequence of the complementarity domain is sufficiently complementary to a portion of the nucleotide sequence of the target DNA to permit hybridization of the RNA probe to the target polynucleotide. Optionally, the length of the complementarity domain of the RNA probe is ≥10 nucleotides, optionally ≥17 nucleotides, and of sufficient length to ensure specific hybridization with the target DNA. Optionally, the length of the complementarity domain of the RNA probe is from about 10 to about 100 nucleotides, optionally about 17 to about 40 nucleotides. Optionally, the the length of the domain of the RNA probe is integer between 10 and 100 nucleotides, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100. By "sufficient length" it is meant an oligonucleotide of greater than or equal to 10 nucleotides, optionally greater than or equal to 17 nucleotides, that is of a length great enough to provide the intended hybridisation of the RNA probe to the DNA target under the appropriate conditions. Optionally, the nucleotide sequence of the complementarity domain of the RNA probe on the RNA-functionalised metal nanoparticle and the nucleotide sequence of at least a portion of the target DNA is at least about 50% complementary, optionally at least about 60% complementary, optionally at least about 70% complementary, optionally at least about 80% complementary, optionally at least about 90% complementary, optionally at least about 95% complementary, optionally 100% complementary, to permit hybridization of the target DNA and the RNA probe.

Optionally, the RNA probe has a nucleotide sequence comprising 5'-AGG UGU GGA CGA CGU CAA GUC AUC AUG-3' (SEQ ID NO: 1), or a nucleotide sequence having 50%, optionally 60%, optionally 70%, optionally 80%, optionally 90%, optionally 95%, optionally 100%, sequence similarity to the sequence 5'-AGG UGU GGA CGA CGU CAA GUC AUC AUG-3' (SEQ ID NO: 1). Optionally, the RNA probe has a suitable moiety at the 5' end, optionally at the 3' end, of the RNA probe to facilitate coupling of the RNA probe to a suitable modification, optionally an amine modification, a sulfide modification, a disulfide modification, a thiol modification, or a dithiol modification, and thus subsequent conjugation to a metal nanoparticle. Optionally, the RNA probe has an amino ($NH_2$) moiety at the 5' end, optionally at the 3' end, of the RNA probe. Optionally, the RNA probe has a moiety comprising an amino ($NH_2$) group and a C6, C7, C8, C9, C10, C11, C12 or C13-C20 spacer arm at the 5' end, optionally at the 3' end, of the RNA probe. Optionally, the RNA probe has a nucleotide sequence comprising 5'-Amino-C6-AGG UGU GGA CGA CGU CAA GUC AUC AUG-3' (i.e. an amino-C6 moiety at the 5' end of SEQ ID NO: 1). Optionally, the RNA probe has a nucleotide sequence consisting of 5'-Amino-C6-AGG UGU GGA CGA CGU CAA GUC AUC AUG-3' (i.e. an amino-C6 moiety at the 5' end of SEQ ID NO: 1).

The amino-C6 moiety, appended to the 5' $PO_3$— group in the RNA probe, may be illustrated as

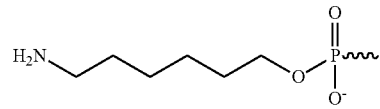

Optionally, the amino moiety, and optionally the C6, C7, C8, C9, C10, C11, C12 or C13-C20 spacer arm, can be added the 3'-end of the RNA probe using any suitable means known in the art, such as a 3'-amino-modified solid support. Optionally, the amino moiety, and optionally the C6, C7, C8, C9, C10, C11, C12 or C13-C20 spacer arm, can be added the 5'-end of the RNA probe post-synthetically using any suitable means known in the art. Without wishing to be bound by theory, it is understood that, for a thioctic acid-modified RNA probe, the amino moiety facilitates coupling of the RNA probe to the NHS group of the thioctic acid-modification, and thus subsequent conjugation to a metal nanoparticle.

Optionally, the metal nanoparticles are colloidal metal nanoparticles. Optionally, prior to functionalization, the metal nanoparticles are suspended in a suitable buffer. Optionally, prior to functionalization, the metal nanoparticles are suspended in a sodium citrate buffer. Optionally, the metal nanoparticles are reduced and stored in a sodium citrate buffer. Optionally, each metal nanoparticle has a shape selected from a sphere, rod, a polygonal rod, rectangular block, cube, tetrapod, and pyramid. Optionally, each metal nanoparticle is in the shape of a sphere. Without wishing to be bound by theory, it is understood that sphere-shaped metal nanoparticles provide for more simple synthesis, RNA functionalization, and/or improved localized surface plasmon resonance (LSPR) properties compared to other shapes of metal nanoparticles. Optionally, a non-functionalised metal nanoparticle has a mean diameter of about 1-100 nm, optionally about 10-100 nm, optionally about 10-50 nm, optionally about 10-25 nm, optionally about 10-20 nm, further optionally about 17 nm. Optionally, a functionalised metal nanoparticle has a mean diameter of about 20-200 nm, optionally about 20-100 nm, optionally about 30-60 nm, optionally about 40-50 nm, further optionally about 44.4 nm. Optionally, an aggregated mass of metal nanoparticles has a mean diameter of about 100-1000 nm, optionally about 500-1000 nm, optionally about 750-1000 nm, optionally about 800-900 nm, further optionally about 854 nm.

Optionally, the heteroduplex comprising the target DNA and the RNA probe on the RNA-functionalised metal nanoparticle is formed under conditions suitable for formation of an RNA-DNA heteroduplex. Optionally, the heteroduplex comprising the target DNA and the RNA probe on the RNA-functionalised metal nanoparticle is formed under suitable buffer conditions, and optionally suitable temperature conditions and/or suitable lengths of time, for formation of an RNA-DNA heteroduplex. Suitable buffer conditions are known to the person skilled in the art, and can comprise any suitable buffers which condition allow for specific hybridisation of the target DNA and the RNA probe on the RNA-functionalised metal nanoparticle. Optionally, suitable buffer conditions comprise a Tris-HCl buffer, optionally a modified Tris-HCL buffer. Optionally, the modified Tris-HCL buffer comprises 20 mM Tris (2-Amino-2-(hydromethyl)propane-1,3-diol), 40 mM KCl (potassium chloride), 8 mM $MgCl_2$ (magnesium chloride), 1 mM DTT (1,4-Dithiothreitol), and, optionally, 30 µM GSH (glutathione), wherein the pH is adjusted with HCl (hydrochloric acid) to about pH 7. Optionally, once the double-stranded DNA has been dissociated to single-stranded DNA, the sample is cooled to a temperature of about 40° C. to about 70° C., optionally about 40° C. to about 60° C., optionally at a temperature of about 50° C. to 60° C., optionally at a temperature of about 60° C. Optionally, said cooling occurs over a period of about 1 second to about 1 hour, optionally about 30 seconds to about 30 minutes, optionally about 1 minute to about 20 minutes, optionally about 1 minute to about 10 minutes. Optionally, the heteroduplex comprising the target DNA and the RNA probe on the RNA-functionalised metal nanoparticle is formed by maintaining the sample at a suitable temperature wherein the suitable temperature is about 40° C. to about 70° C., optionally about 40° C. to about 60° C., optionally about 50° C. to 60° C., optionally about 60° C. Optionally, the heteroduplex comprising the target DNA and the RNA probe on the RNA-functionalised metal nanoparticle is formed by maintaining the sample at a suitable temperature for about 0.5 hours to about 2 hours, optionally for about 0.5 hours to about 1.5 hours, optionally for about 1 hour. Optionally, the nucleotide sequence of the complementarity domain of the RNA probe on the RNA-functionalised metal nanoparticle and the nucleotide sequence of at least about a portion of the target DNA is sufficiently complementary to permit hybridization of the target DNA and the RNA probe under conditions suitable for formation of an RNA-DNA heteroduplex, wherein said conditions are as defined above.

Optionally, the heteroduplex of target DNA and the RNA probe on the RNA-functionalised metal nanoparticle is contacted with an enzyme under conditions suitable for the enzyme to cleave the RNA probe in the heteroduplex thereby releasing the DNA. Optionally, the heteroduplex of target DNA and the RNA probe on the RNA-functionalised metal nanoparticle is contacted with an enzyme under suitable buffer conditions, and optionally suitable temperature conditions and/or suitable lengths of time, for the enzyme to cleave the RNA probe in the heteroduplex thereby releasing the DNA. Suitable buffer conditions are known to the person skilled in the art, and can comprise any suitable buffers which allow for the enzyme to cleave the RNA probe in the heteroduplex thereby releasing the DNA. Optionally, suitable buffer conditions comprise a Tris-HCl buffer, optionally a modified Tris-HCL buffer. Optionally, the modified Tris-HCL buffer comprises 20 mM Tris (2-Amino-2-(hydroxymethyl)propane-1,3-diol), 40 mM KCl (potassium chloride), 8 mM $MgCl_2$ (magnesium chloride), 1 mM DTT (1,4-Dithiothreitol), and, optionally, 30 µM GSH (glutathione), wherein the pH is adjusted with HCl (hydrochloric acid) to about pH 7. Optionally, the heteroduplex of target DNA and the RNA probe on the RNA-functionalised metal nanoparticle is contacted with an enzyme for a time sufficient for the enzyme to cleave the RNA probe in the heteroduplex thereby releasing the DNA. Optionally, the heteroduplex of target DNA and the RNA probe on the RNA-functionalised metal nanoparticle is contacted with the enzyme for a suitable time sufficient for the enzyme to cleave the RNA probe in the heteroduplex, wherein said suitable time is at least about 1 minute, optionally at least about 10 minutes, optionally at least about 20 minutes, optionally at least about 30 minutes, optionally at least about 40 minutes, optionally at least about 50 minutes, optionally at least about 1 hours, thereby releasing the DNA. Optionally, the heteroduplex of target DNA and the RNA probe on the RNA-functionalised metal nanoparticle is contacted with the enzyme at a temperature suitable to cleave the RNA probe in the heteroduplex thereby releasing the DNA. Optionally, the heteroduplex of target DNA and the RNA probe on the RNA-functionalised metal nanoparticle is contacted with the enzyme at a temperature of at least about 15° C., optionally at least about 20° C., optionally at least about 25° C., optionally at least about 30° C., optionally at least about 37° C. Optionally, the enzyme is an enzyme that cleaves phosphodiester bonds in the RNA probe in the DNA-RNA heteroduplex. In other words, the enzyme is an enzyme that specifically cleaves the phosphodiester bonds of the RNA oligonucleotide probe when said RNA probe is in a DNA-RNA heteroduplex, i.e. a heteroduplex comprising the target DNA and the RNA probe. Optionally, the enzyme is a ribonuclease enzyme that cleaves phosphodiester bonds in the RNA probe in the DNA-RNA heteroduplex. Optionally, the enzyme is RNase H. Optionally, the final concentration of enzyme, optionally ribonuclease enzyme, optionally RNase H, used to cleave the RNA probe in the heteroduplex thereby releasing the DNA is about 0.01 U to 0.1 U, optionally 0.01 U to 0.05 U, optionally about 0.02 U. Optionally, in step (c), the heteroduplex of target DNA and the RNA probe on the RNA-functionalised metal nanoparticle is contacted with RNase H at a temperature of about 37° C. for about 1 hour.

Optionally, at least steps (c) and (d) are carried out at substantially the same temperature. Optionally, at least steps (c) and (d) are carried out at substantially the same, and substantially constant, temperature. Optionally, at least steps (c) and (d) are carried out under substantially isothermal conditions. Optionally, steps (a) to (e) are carried out under substantially isothermal conditions.

Optionally, steps (b) and (c) are repeated until substantially all of the RNA probes on the RNA-functionalised metal nanoparticles have been cleaved from the metal nanoparticles. Optionally, steps (b) and (c) are repeated until at least about 50%, optionally at least about 60%, optionally at least about 70%, optionally at least about 80%, optionally at least about 90%, optionally at least about 95%, optionally at least about 96%, optionally at least about 97%, optionally at least about 98%, optionally at least about 99%, of the RNA probes have been cleaved from the metal nanoparticles. Optionally, steps (b) and (c) are repeated until 100% of the RNA probes have been cleaved from the metal nanoparticles. It is understood that the extent to which the RNA probes on the RNA-functionalised metal nanoparticles have been cleaved from the metal nanoparticles will correlate with the level of stability of the functionalised metal nanoparticles, and the extent of aggregation of the metal nanoparticles under increased electrolytic content, such an increased NaCl content, of a medium containing the metal nanoparticles and thus colorimetric response.

Optionally, the metal nanoparticles from which all, or substantially all, of the RNA probes have been cleaved are aggregated by increasing the electrolytic content of a medium containing the metal nanoparticles. Optionally, the medium is a medium comprising the sample which comprised the target DNA, and optionally in which the functionalised metal particles contacted the target DNA, and/or optionally in which the enzyme cleaved RNA in a DNA-RNA heteroduplex thereby releasing the target DNA. Optionally, the electrolytic content of the medium is increased by the addition of a salt. Optionally, the electrolytic content of the medium is increased by the addition of sodium chloride (NaCl), potassium chloride (KCl), calcium chloride ($CaCl_2$), magnesium chloride ($MgCl_2$), or manganese(II) chloride ($MnCl_2$) or mixtures thereof, optionally by the addition of NaCl. Optionally, the electrolytic content of the medium is increased by the addition of a salt, optionally the addition of NaCl, to a final concentration of at least about 1 M, optionally at least about 2 M.

Optionally, the target DNA in the sample comprises animal, optionally human, DNA. Optionally, the target DNA in the sample comprises microbial, optionally bacterial, DNA. Optionally, the target DNA in the sample comprises pathogenic, optionally pathogenic microbial, DNA. Optionally, the target DNA in the sample comprises *Campylobacter jejuni* DNA. Optionally, the sample comprises a sample obtained from an animal, optionally a human. Optionally, the sample comprises a bodily fluid, secretion and or cell, such as bodily fluids, secretions, and cells, such as blood, saliva, sweat, hair, mucus, cerebrospinal fluid, urine, and faeces, obtained from an animal, optionally a human. Optionally, the sample comprises a food sample. Optionally, the food sample comprises meat, vegetable, grain, or other foodstuff. Optionally, the sample is suspended in a suitable buffer, optionally a Tris-HCl buffer, optionally a modified Tris-HCl buffer as defined above. Optionally, the sample comprises a food sample comprising, or potentially comprising, pathogenic microbial DNA, optionally *Campylobacter jejuni* DNA. Optionally, the target DNA in the sample comprises the sequence 5'-CAT GAT GAC TTG ACG TCG TCC ACA CCT-3' (SEQ ID NO: 2), or a sequence having 50%, optionally 60%, optionally 70%, optionally 80%, optionally 90%, optionally 95%, optionally 96%, optionally 97%, optionally 98%, optionally 99%, optionally 100%, sequence similarity to the sequence 5'-CAT GAT GAC TTG ACG TCG TCC ACA CCT-3' (SEQ ID NO: 2).

Optionally, the limit of detection (LOD) of the method described herein is about ≤1 pM, optionally ≤100 fM, optionally ≤40.7 fM, optionally ≤10 fM, optionally ≤2.45 fM, optionally ≤1 fM concentration of target DNA in the sample. Optionally, the limit of detection (LOD) of the method described herein is 40.7 fM when a colour change as a result of aggregation of metal nanoparticles is measured by UV-visible light spectrophotometer. Optionally, the limit of detection (LOD) of the method described herein is 2.45 fM when an average size of the metal nanoparticles conjugates is measured by dynamic light scattering (DLS). Optionally, the limit of detection (LOD) of the method described herein, when used to detect DNA in a food sample, is 1.2 pM when a colour change as a result of aggregation of metal nanoparticles is measured by UV-visible light spectrophotometer. Optionally, the limit of detection (LOD) of the method described herein, when used to detect DNA in a food sample, is 18 fM when an average size of the metal nanoparticles conjugates is measured by dynamic light scattering (DLS), Optionally, the target DNA is present in the sample at a concentration of less than about 1 fM, optionally less than about 10 fM, optionally less than about 100 fM, optionally less than about 1 pM, optionally less than about 10 pM, optionally less than about 100 pM, optionally less than about 1 nM, optionally less than about 10 nM, optionally less than about 100 nM, optionally less than about 1 pM, optionally less than about 10 µM, optionally less than about 100 µM, optionally less than about 1 mM.

Optionally, aggregation of the metal nanoparticles causes the metal nanoparticles to change colour thereby indicating the presence of the target DNA. Optionally, the metal nanoparticles comprise gold nanoparticles. Optionally, aggregation of the gold nanoparticles causes the gold nanoparticles to change colour from red to blue thereby indicating the presence of the target DNA strand. Optionally, aggregation of the gold nanoparticles causes the gold nanoparticles change its light emission wavelength from about 525 nm, corresponding to RNA-functionalised gold nanoparticles, to a wavelength greater than 525 nm, optionally to a wavelength of at least about 530 nm, optionally to a wavelength of at least about 535 nm, optionally to a wavelength of at least about 540 nm, optionally to a wavelength of at least about 545 nm, optionally to a wavelength of at least about 550 nm, optionally to a wavelength of at least about 555 nm, corresponding to aggregated gold nanoparticles, thereby indicating the presence of the target DNA strand. Optionally, the change of colour of the metal nanoparticles, optionally gold nanoparticles, is detected by the naked eye. Optionally, the change of colour of the metal nanoparticles, optionally gold nanoparticles, is detected spectrophotometrically. Optionally, the change of colour of the metal nanoparticles, optionally gold nanoparticles, is detected using a spectrophotometer, optionally an ultraviolet (UV)-visible light spectrophotometer. Optionally, aggregation of the metal nanoparticles, optionally gold nanoparticles, is detected using transmission electron microscopy. Optionally, aggregation of the metal nanoparticles, optionally gold nanoparticles, is detected using a dynamic light scattering technique.

In a further aspect, the invention provides a kit for detecting a target DNA in a sample, wherein the kit is used according to the method of the invention described herein. Optionally, the kit comprises a plurality of metal nanoparticles and one or more RNA probes suitable for the detection of the target DNA. Optionally, the kit comprises a plurality of metal nanoparticles functionalised with one or more RNA probes suitable for the detection of the target DNA.

Optionally, the metal nanoparticles comprise noble metal nanoparticles. Optionally, the metal nanoparticles consist of noble metal nanoparticles. Optionally, the metal nanoparticles comprise a mixture of different types of noble metal nanoparticles. Alternatively, the metal nanoparticles comprise the same, or substantially the same, type of noble metal nanoparticles. Optionally, the metal nanoparticles are selected from one of more of gold nanoparticles, silver nanoparticles, platinum nanoparticles, copper nanoparticles, palladium nanoparticles, ruthenium nanoparticles, rhodium nanoparticles, osmium nanoparticles, and iridium nanoparticles, or alloys of these metals. Optionally, the metal nanoparticles are gold nanoparticles.

Optionally, the metal nanoparticles are functionalised with one or more RNA probes, wherein the one or more RNA probes are conjugated, optionally covalently conjugated, to each metal nanoparticle. Optionally, the metal nanoparticles are functionalised with one or more RNA probes, wherein the one or more RNA probes are conjugated, optionally covalently conjugated, to each metal nanoparticle via a modification at the 5' end, alternatively at the 3' end, of the one or more RNA probes. A suitable modification is well known to the person skilled in the art and may be, for example, an amine modification, a sulfide modification, a disulfide modification, a thiol modification, or a dithiol modification at the 5' end, alternatively at the 3' end, of each RNA probe. Optionally, the metal nanoparticles are functionalised with one or more amine-modified RNA probes, wherein the one or more amine-modified RNA probes are conjugated, optionally covalently conjugated, to each metal nanoparticle. In other words, each of the one or more RNA probes are conjugated to the metal nanoparticles through an amine linkage. Optionally, the metal nanoparticles are functionalised with one or more sulfide-modified RNA probes, wherein the one or more sulfide-modified RNA probes are conjugated, optionally covalently conjugated, to each metal nanoparticle. In other words, each of the one or more RNA probes are conjugated to the metal nanoparticles through a sulfide linkage. Optionally, the metal nanoparticles are functionalised with one or more disulfide-modified RNA probes, wherein the one or more disulfide-modified RNA probes are conjugated, optionally covalently conjugated, to each metal nanoparticle. In other words, each of the one or more RNA probes are conjugated to the metal nanoparticles through a disulfide linkage. Optionally, the metal nanoparticles are functionalised with one or more thiol-modified RNA probes, wherein the one or more thiol-modified RNA probes, optionally alkanethiol-modified RNA probes, are conjugated, optionally covalently conjugated, to each metal nanoparticle. In other words, each of the one or more RNA probes are conjugated to the metal nanoparticles through a thiol linkage. Optionally, the metal nanoparticles are functionalised with one or more dithiol-modified RNA probes, wherein the one or more dithiol-modified RNA probes are conjugated, optionally covalently conjugated, to each metal nanoparticle. In other words, each of the one or more RNA probes are conjugated to the metal nanoparticles through a dithiol linkage. Optionally, the metal nanoparticles are functionalised with one or more thioctic acid-modified RNA probes, wherein the one or more thioctic acid-modified RNA probes are conjugated, optionally covalently conjugated, to each metal nanoparticle. In other words, each of the one or more RNA probes are conjugated to the metal nanoparticles through a thioctic acid linkage. Optionally, the metal nanoparticles are functionalised with one or more thioctic acid-modified RNA probes, wherein the one or more thioctic acid-modified RNA probes are conjugated to each metal nanoparticle via an N-hydroxysuccimidyl ester of thioctic acid at the 5' end, alternatively at the 3' end, of the RNA probes. Optionally, the metal nanoparticles are functionalised with one or more thioctic acid-modified RNA probes, wherein the one or more thioctic acid-modified RNA probes are conjugated to each metal nanoparticle via an N-hydroxysuccimidyl (NHS) ester of thioctic acid at the 5' end, alternatively at the 3' end, of the RNA probes. Derivatives of thioctic acid, such as reduced thioctic acid, are also suitable for use in modifying RNA probes as described herein. In addition, other sulphides, disulfides and thiols suitable for use in modifying RNA probes as described herein include sulfides in the form of R—S—R, e.g. 3-(Methylthio)-1-propanol), disulfides in the form of R—S—S—R, e.g. bis(10-carboxydecyl)disulphide), and thiols in the form of R—SH, e.g. alkyl thiols, wherein R represents a unsubstituted or substituted group comprising but not limited to an aliphatic or aromatic alkane, alkene, or other carbon-containing group of atoms including, but not limited to, ethylene glycol derivatives, and thiolated ethylene glycol derivatives such [11-(Methylcarbonylthio)undecyl]tetra(ethylene glycol), which modifications can coordinate strongly onto the metal surface. Additional thiol modifications include 1-propanethiol, 1-butanethiol, 1-pentanethiol, 1-hexanethiol, 1-heptanethiol, 1-octanethiol, 1-nonanethiol, 1-decanethiol, 1-undecanethiol, 1-dodecanethiol, 1-tetradecanethiol, 1-pentadecanethiol, 1-hexadecanethiol, 1-octadecanethiol, 2-ethylhexanethiol, 2-methyl-1-propanethiol, 3-methyl-1-butanethiol, butyl 3-mercaptopropionate, tert-dodecylmercaptan, and tert-nonylmercaptan. Additional dithiol modifications include 1,2-ethandithiol, 1,3-propanedithiol, 1,4-butanedithiol, 2,3-butanedithiol, 1,5-pentanedithiol, 1,6-hexanedithiol, 1,8-octanedithiol, 1,9-nonanedithiol, tetra(ethylene glycol) dithiol, hexa(ethylene glycol) dithiol, 2,2'-(ethylenedioxy)diethanethiol, and 5,5'-bis(mercaptomethyl)-2,2'-bipyridine.

Optionally, the RNA probe or the RNA probe on the RNA-functionalised metal nanoparticle is single-stranded DNA.

Optionally, the RNA probe is of sufficient length to allow the probe to hybridise with the DNA target. The RNA probes useful in the methods and kits disclosed herein may be of varying lengths. Optionally, the RNA probe is about 5 to about 200, optionally about 5 to about 100, optionally about 5 to about 75, optionally about 10 to about 50, further optionally about 17 to about 40, nucleotides in length. Optionally, the RNA probe, as disclosed herein, comprises a complementarity domain, which domain comprises part of, or the whole, of the nucleotide sequence of the RNA probe. Optionally, the nucleotide sequence of the complementarity domain is sufficiently complementary to a portion of the nucleotide sequence of the target DNA to permit hybridization of the RNA probe to the target polynucleotide. Optionally, the length of the complementarity domain of the RNA probe is ≥10 nucleotides, optionally ≥17 nucleotides, and of sufficient length to ensure specific hybridization with the target DNA. Optionally, the length of the complementarity domain of the RNA probe is from about 10 to about 100 nucleotides, optionally about 17 to about 40 nucleotides. Optionally, the the length of the domain of the RNA probe is integer between 10 and 100 nucleotides, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100. By "sufficient length" it is meant an oligonucleotide of greater than or equal to 10 nucleotides, optionally greater than or equal to 17 nucleotides, that is of a length great enough to provide the intended hybridisation of the RNA probe to the DNA target under the appropriate conditions. Optionally, the nucleotide sequence of the complementarity domain of the RNA probe on the RNA-functionalised metal nanoparticle and the nucleotide sequence of at least a portion of the target DNA is at least about 50% complementary, optionally at least about 60% complementary, optionally at least about 70% complementary, optionally at least about 80% complementary, optionally at least about 90% complementary, optionally at least about 95% complementary, optionally 100% complementary, to permit hybridization of the target DNA and the RNA probe.

Optionally, the RNA probe has a nucleotide sequence comprising 5'-AGG UGU GGA CGA CGU CAA GUC AUC AUG-3' (SEQ ID NO: 1), or a nucleotide sequence having 50%, optionally 60%, optionally 70%, optionally 80%, optionally 90%, optionally 95%, optionally 100%, sequence similarity to the sequence 5'-AGG UGU GGA CGA CGU CAA GUC AUC AUG-3' (SEQ ID NO: 1). Optionally, the RNA probe has a suitable moiety at the 5' end, optionally at the 3' end, of the RNA probe to facilitate coupling of the RNA probe to a suitable modification, optionally an amine modification, a sulfide modification, a disulfide modification, a thiol modification, or a dithiol modification, and thus subsequent conjugation to a metal nanoparticle. Optionally, the RNA probe has an amino (NH$_2$) moiety at the 5' end, optionally at the 3' end, of the RNA probes. Optionally, the RNA probe has a moiety comprising an amino (NH$_2$) group and a C6, C7, C8, C9, C10, C11, C12 or C13-C20 spacer arm at the 5' end, optionally at the 3' end, of the RNA probes. Optionally, the RNA probe has a nucleotide sequence comprising 5'-Amino-C6-AGG UGU GGA CGA CGU CAA GUC AUC AUG-3' (i.e. an amino-C6 moiety at the 5' end of SEQ ID NO: 1). Optionally, the RNA probe has a nucleotide sequence consisting of 5'-Amino-C6-AGG UGU GGA CGA CGU CAA GUC AUC AUG-3' (i.e. an amino-C6 moiety at the 5' end of SEQ ID NO: 1).

The amino-C6 moiety, appended to the 5' PO$_3$— group in the RNA probes, may be illustrated as

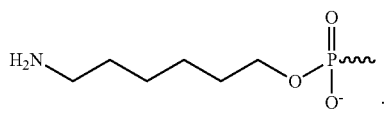

Optionally, the amino moiety, and optionally the C6, C7, C8, C9, C10, C11, C12 or C13-C20 spacer arm, can be added the 3'-end of the RNA probe using any suitable means known in the art, such as a 3'-amino-modified solid support. Optionally, the amino moiety, and optionally the C6, C7, C8, C9, C10, C11, C12 or C13-C20 spacer arm, can be added the 5'-end of the RNA probe post-synthetically using any suitable means known in the art.

Optionally, the metal nanoparticles are colloidal metal nanoparticles. Optionally, prior to functionalization, the metal nanoparticles are suspended in a suitable buffer. Optionally, prior to functionalization, the metal nanoparticles are suspended in a sodium citrate buffer. Optionally, the metal nanoparticles are reduced and stored in a sodium citrate buffer. Optionally, each metal nanoparticle has a shape selected from a sphere, rod, a polygonal rod, rectangular block, cube, tetrapod, and pyramid. Optionally, each metal nanoparticle is in the shape of a sphere. Optionally, a non-functionalised metal nanoparticle has a mean diameter of about 1-100 nm, optionally about 10-100 nm, optionally about 10-50 nm, optionally about 10-25 nm, optionally about 10-20 nm, further optionally about 17 nm. Optionally, a functionalised metal nanoparticle has a mean diameter of about 20-200 nm, optionally about 20-100 nm, optionally about 30-60 nm, optionally about 40-50 nm, further optionally about 44.4 nm. Optionally, an aggregated mass of metal nanoparticles has a mean diameter of about 100-1000 nm, optionally about 500-1000 nm, optionally about 750-1000 nm, optionally about 800-900 nm, further optionally about 854 nm.

Optionally, the target DNA to be detected by the kit comprises animal, optionally human, DNA. Optionally, the target DNA to be detected by the kit comprises microbial, optionally bacterial, DNA. Optionally, the target DNA to be detected by the kit comprises pathogenic, optionally pathogenic microbial, DNA. Optionally, the target DNA to be detected by the kit comprises *Campylobacter jejuni* DNA. Optionally, the target DNA to be detected by the kit is comprised in a sample obtained from an animal, optionally a human. Optionally, the sample comprises a bodily fluid, secretion and or cell, such as bodily fluids, secretions, and cells, such as blood, saliva, sweat, hair, mucus, cerebrospinal fluid, urine, and faeces, obtained from an animal, optionally a human. Optionally, the target DNA to be detected by the kit is comprised in a food sample. Optionally, the food sample comprises a meat-based foodstuff such as chicken, vegetable-based foodstuff, and/or grain-based foodstuff. Optionally, the kit comprises a suitable buffer for suspending the sample, optionally the suitable buffer is a Tris-HCl buffer, optionally a modified Tris-HCl buffer as defined above. Optionally, the target DNA to be detected by the kit is comprised in a food sample comprising, or potentially comprising, pathogenic microbial DNA, optionally *Campylobacter jejuni* DNA. Optionally, the target DNA to be detected by the kit comprises the sequence 5'-CAT GAT GAC TTG ACG TCG TCC ACA CCT-3' (SEQ ID NO: 2), or a sequence having 50%, optionally 60%, optionally 70%, optionally 80%, optionally 90%, optionally 95%, optionally 96%, optionally 97%, optionally 98%, optionally 99%, optionally 100%, sequence similarity to the sequence 5'-CAT GAT GAC TTG ACG TCG TCC ACA CCT-3' (SEQ ID NO: 2).

Optionally, the limit of detection (LOD) of the kit, optionally wherein the kit used according to the method described herein, is about ≤1 pM, optionally ≤100 fM, optionally ≤40.7 fM, optionally ≤10 fM, optionally ≤2.45 fM, optionally ≤1 fM concentration of target DNA in the sample, Optionally, the limit of detection (LOD) of the kit, optionally wherein the kit used according to the method described herein, is 40.7 fM when a colour change as a result of aggregation of metal nanoparticles is measured by UV-visible light spectrophotometer. Optionally, the limit of detection (LOD) of the kit, optionally wherein the kit used according to the method described herein, is 2.45 fM when an average size of the metal nanoparticles conjugates is measured by dynamic light scattering (DLS). Optionally, the limit of detection (LOD) of the kit, optionally wherein the kit used according to the method described herein, when used to detect DNA in a food sample is 1.2 pM when a colour change as a result of aggregation of metal nanoparticles is measured by UV-visible light spectrophotometer. Optionally, the limit of detection (LOM) of the kit, optionally wherein the kit used according to the method described herein, when used to detect DNA in a food sample is 18 fM when an average size of the metal nanoparticles conjugates is measured by dynamic light scattering (DLS).

Optionally, the target DNA is present in a sample to be tested by the kit at a concentration of less than about 1 fM, optionally less than about 10 fM, optionally less than about 100 fM, optionally less than about 1 pM, optionally less than about 10 pM, optionally less than about 100 pM, optionally less than about 1 nM, optionally less than about 10 nM, optionally less than about 100 nM, optionally less than about 1 μM, optionally less than about 10 μM, optionally less than about 100 μM, optionally less than about 1 mM.

Optionally, the kit further comprises an enzyme that cleaves RNA in a DNA-RNA heteroduplex. Optionally, the kit further comprises an enzyme that cleaves phosphodiester bonds in the RNA probe when the RNA probe is in a DNA-RNA heteroduplex. Optionally, the kit further comprises a ribonuclease enzyme that cleaves phosphodiester bonds in the RNA probe when the RNA probe is in a DNA-RNA heteroduplex. Optionally, the enzyme is RNase H.

Optionally, the kit comprises a salt. Optionally, the kit comprises NaCl, KCl, $CaCl_2$, $MgCl_2$, or $MnCl_2$, or mixtures thereof. Optionally, the salt is a solution of NaCl, KCl, $CaCl_2$, $MgCl_2$, or $MnCl_2$, or mixtures thereof, wherein optionally the salt solution has a concentration of about 1 to about 10 M, optionally about 1 to about 10 M, optionally about 4 M. Optionally, the salt is a solution of NaCl, wherein optionally the solution of NaCl has a concentration of about 1 to about 10 M, optionally about 1 to about 10 M, optionally about 4 M.

Optionally, the kit further comprises instructions for using the kit. Optionally, the kit further comprises instructions for using the kit according to the method for detecting a target DNA in a sample as described herein.

By "about", as used herein, it is meant that the recited value may be precisely the recited value, optionally ±10% of the recited value, further optionally ±20% of the recited value.

By "some", as used herein, it is meant that the quantity of feature is at least about 20%, optionally at least about 30%, optionally at least about 40%, optionally at least about 50%, of the total quantity of that feature.

By "substantially all", as used herein, it is meant that the quantity of feature is at least greater that about 50%, optionally at least about 60%, optionally at least about 70%, optionally at least about 80%, optionally at least about 90%, optionally at least about 95%, optionally at least about 96%, optionally at least about 97%, optionally at least about 98%, optionally at least about 99%, of the total quantity of that feature.

By "immediately", as used herein, it is meant that a method step is performed subsequent to a preceding method step and within at least about 60 seconds, optionally at least about 30 seconds, optionally at least about 20 seconds, optionally at least about 10 seconds, optionally at least about 1 seconds, optionally at least about 1 second, of the preceding method step.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present invention will now be described, by way of example, with reference to the accompanying drawings, in which.

DETAILED DESCRIPTION

Figure 1:
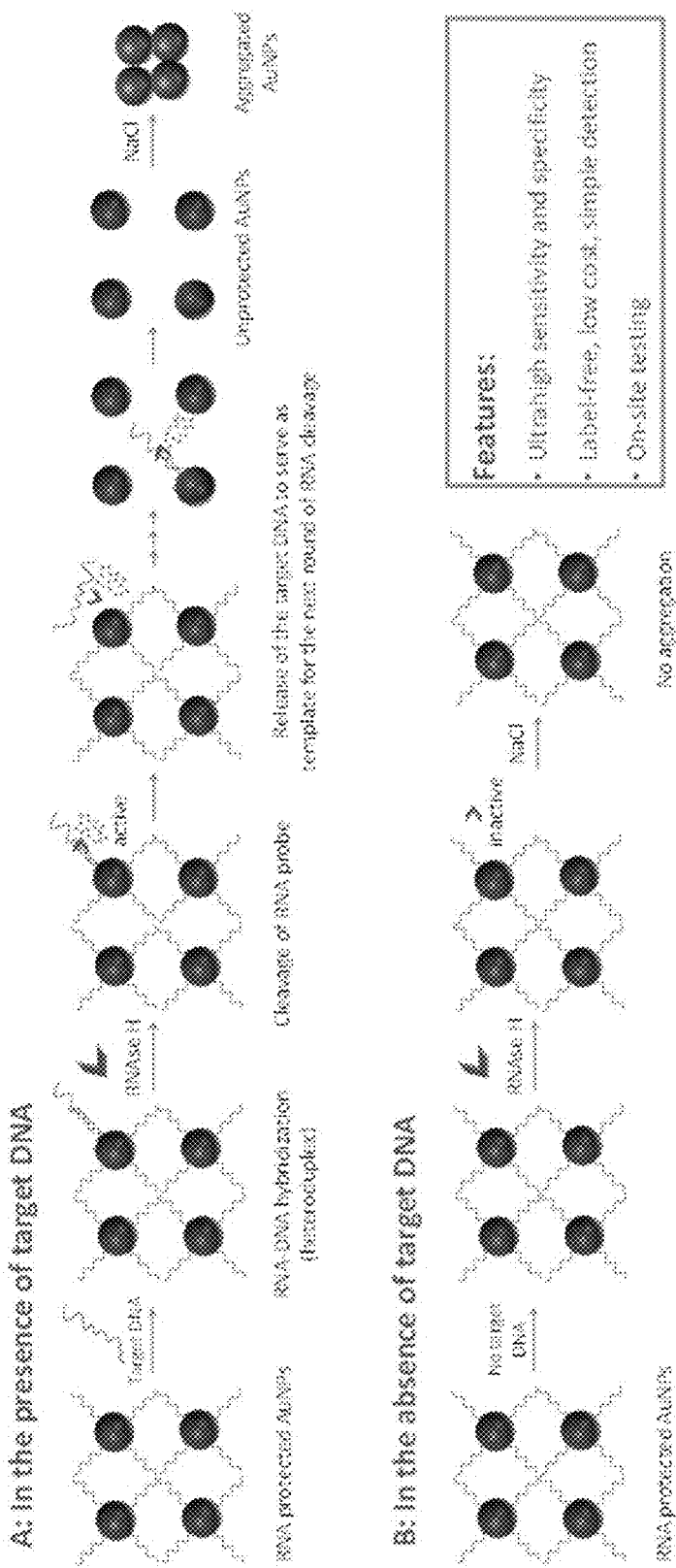
FIG. 1 depicts the overall scheme of the method of the invention and demonstrates the colorimetric detection of target DNA based on DNA-RNA hybridization and enzyme controlled cleavage and aggregation of gold nanoparticles (AuNPs) upon the addition of NaCl. (A) In the presence of target DNA, DNA-RNA hybridization occurs which initiates RNAse H enzyme cleavage of RNA within the heteroduplex structure. The target DNA recycles until all of the RNA is cleaved, allowing for subsequent AuNP aggregation in the presence of NaCl. (B) In the absence of target DNA, no hybridization occurs, thus there is no heteroduplex structure to act on and the RNAse H enzyme is inactive. Therefore, the particles remain stable upon the addition of NaCl.

Embodiments of the present invention will now be described with reference to the following non-limiting examples:

Methods

Materials:

$NH_2$ RNA probe (5'-Amino-C6-AGG UGU GGA CGA CGU CAA GUC AUC AUG-3') (SEQ ID NO: 1), complementary DNA sequence (5'-CAT GAT GAC TTG ACG TCG TCC ACA CCT-3') (SEQ ID NO: 2), non-complementary DNA sequence 1 (5'-CCA ACC CCC CAG AAA GAA-3') (SEQ ID NO: 3) and non-complementary sequence 2 (5'-TCT ATT GGT GGT AAA ACT TAC GCT GCA AGT AAA GCC GAA GGT CAC-3') (SEQ ID NO: 4) were purchased from Eurofins Genomics (Ebersburg, Germany). RNAse H enzyme was purchased from Takara Bio (France) and thioctic acid NHS ester from Link Technology Ltd. (UK). Sodium citrate tribasic dehydrate (HOC(COONa)($CH_2COONa)_2 \cdot 2H_2O$), gold (III) chloride ($HAuCl_4$), dimethyl sulfoxide (DMSO) (($CH_3)_2SO$), Tween$_{20}$, sodium chloride (NaCl), sodium carbonate ($Na_2CO_3$), sodium bicarbonate ($Na_2HCO_3$), triethylammonium acetate buffer (TEAA), sodium phosphate ($NaH_2PO_4$ and $Na_2HPO_4$), glutathione (GSH), Tris-EDTA buffer (TE), Tris-HCl ($NH_2C(CH_2OH)_3$), hydrochloric acid (HCl), potassium chloride (KCl), magnesium chloride ($MgCl_2$) and dithiothreitol (DTT) were purchased from Sigma-Aldrich (UK). All reagents were prepared in RNAse free water (Sigma, UK). NAP-5 column was obtained from GE Healthcare (UK). Syringe filters (0.22 µm) were purchased from Merck Millipore (Germany).

Gold Nanoparticle Synthesis:

In a typical experiment, 25 mM $HAuCl_4$ was dissolved in 150 mL d$H_2O$ and heated to reflux under constant stirring (t=~10 minutes). 1 mL 2.4 mM of sodium citrate was quickly injected and the solution was removed from the heat upon the colour changed from translucent yellow to wine red. The pH of the solution was adjusted to 6.5 using HCl.

RNA Preparation:

Prior to functionalization, the RNA was modified with thiotic acid at the 5' end. The dried RNA was incubated with thiotic acid/80 mM DMSO (30 µL) and $Na_2CO_3$/NaHCO$_3$ (75 µL) overnight at room temperature. The modified RNA was desalted using a NAP-5 column in TEAA buffer (0.1 M). The concentration was determined using Nanodrop 8000 (Thermoscientific, UK).

Gold Nanoparticle Functionalization:

Gold nanoparticles were functionalized with RNA. Typically, 300 µL of 30 µM modified-RNA was added to 1 mL AuNP solution. The solution was incubated overnight (t=~16 hours) at room temperature and stability checked with 4 M NaCl (2 M). To improve the orientation of the RNA conjugated onto the surface of the AuNP, the salt concentration was slowly increased. Firstly, phosphate buffer (60 mM) was diluted to a final concentration of 10 mM. NaCl was added in small increments (0.05 M) each hour, over six hours (0.3 M). The conjugate was incubated overnight (t=~16 hours) at room temperature. Finally, the conjugate was centrifuged twice at 13,000 g for 1 hour to remove unbound RNA and re-suspended in TE buffer (stored at 4° C.).

Determination of AuNP-RNA Stability:

In order to ensure the colloidal stability of the RNA-functionalized AuNPs at high salt concentrations, the conjugates were exposed to different concentrations of NaCl (Figure SI. 2). The functionalized particles exhibit excellent stability at 2 M NaCl, with no wavelength shift noted. The bare-AuNPs immediately aggregated at 0.5 M NaCl, due to the large screening effect of NaCl, causing a red-shift to longer wavelengths on the absorbance spectrum ($\lambda_{max}$ shift >200 nm). This stability can be attributed to electrostatic repulsion or steric exclusion caused by RNA on the AuNP surface. From this analysis, successful functionalisation was confirmed and 2 M NaCl was set as the highest concentration to induce aggregation of AuNPs over varying stabilities.

Colorimetric Detection of Pathogenic Bacterial DNA:

Prior to analysis, the AuNP conjugate was centrifuged (13,000 g for 30 min) and re-suspended in a modified Tris-HCl buffer (20 mM Tris, 40 mM KCl, 8 mM $MgCl_2$ and 1 mM DTT). 30 µM GSH was also added to this buffer due to its role in aiding RNAse H enzyme activity. In a typical experiment, 20 µL of AuNP-RNA was added into an Eppendorf tube with 10 µL of target DNA or control (modified Tris-buffer) and 1.5 µL of Tween20. The sample was heated to 90° C. for 2 minutes, cooled slowly to 60° C. and incubated at 60° C. for 1 hour. 0.06 U of RNAse H enzyme, prepared in modified Tris-buffer, was added to a final concentration of 0.02 U. The sample was then incubated for 1 hour at 37° C. To induce aggregation, NaCl was added to a final, effective concentration of 2 M.

Preparation of DNA in Chicken Matrix:

50 g of skinless chicken meat (breast) was shaken for 2 minutes in 100 mM Tris-HCl (pH 7). The subsequent matrix was filtered and diluted 1/100 in modified Tris-HCl buffer (20 mM Tris, 40 mM KCl, 8 mM $MgCl_2$ and 1 mM DTT). This matrix was then used to prepare a 10-fold dilution of target DNA ranging from 0 to 10 µM concentration.

Analysis Instrumentation:

All Ultraviolet-visible spectrophotometry measurements were carried out using a Cary 60 spectrophotometer (Agilent Technologies, USA). AuNP size analysis was carried out using a Zetasizer NanoZS (Malvern, UK). Transmission electron microscopy (TEM) characterization was acquired using a Phillips CM100 (Phillips, USA) operated at 100 kV.

Results & Discussion

Figure 2:
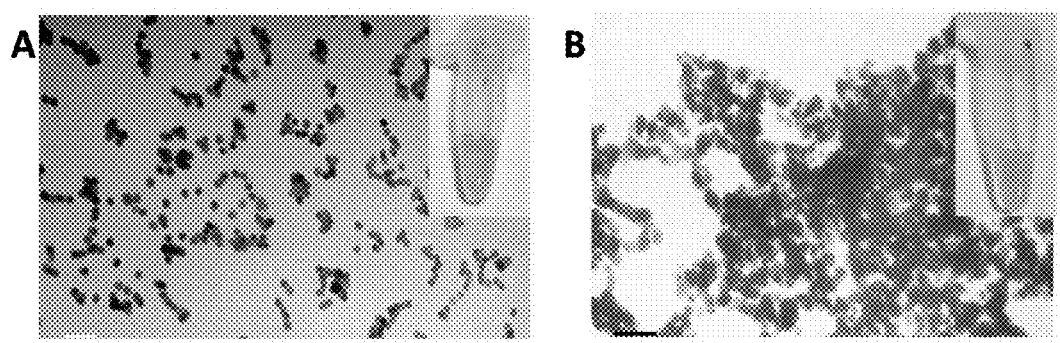
FIG. 2 depicts transmission electron microscopy (TEM) images and photographs of the colorimetric response of AuNPs in the (A) absence and (B) presence of target DNA (1 μM) post assay conditions. Scale bar=100 nm.
Figure 7:
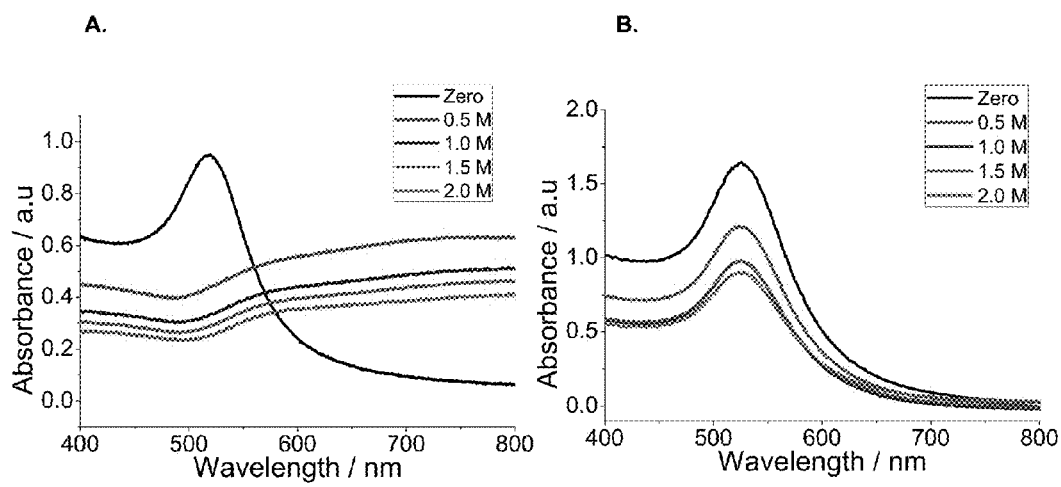
FIG. 7 depicts the stability of RNA-AuNP conjugates (A) and bare nanoparticles (B) following additional of different concentrations of NaCl (zero to 2.0 M), further demonstrating successful functionalisation and determination of assay conditions.
Figure 8:
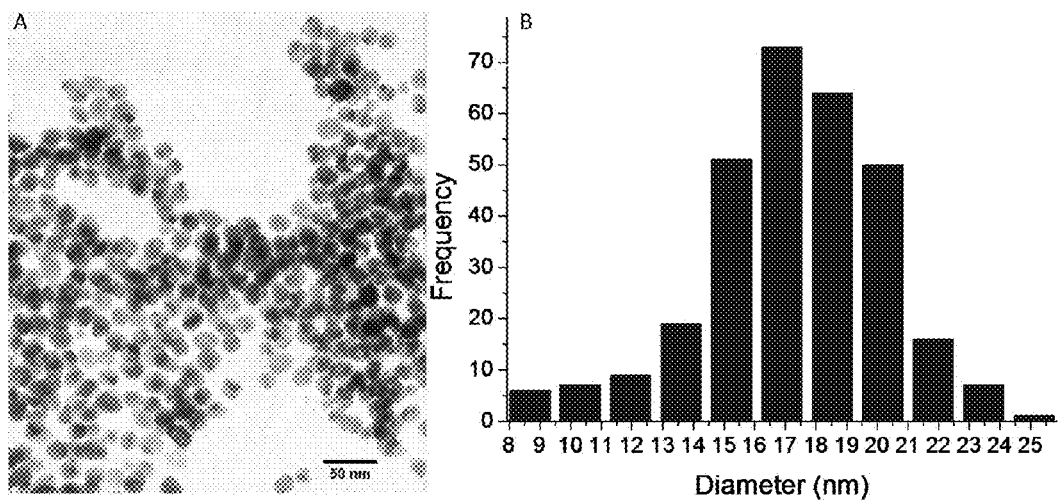
FIG. 8 depicts the results of gold nanoparticle (AuNP) characterization. The figures illustrate transmission electron microscopy (TEM) characterization of AuNPs produced via the citrate reduction/Turkevich method (A) and size distribution analysis of the particles using ImageJ software (B).
Figure 9:
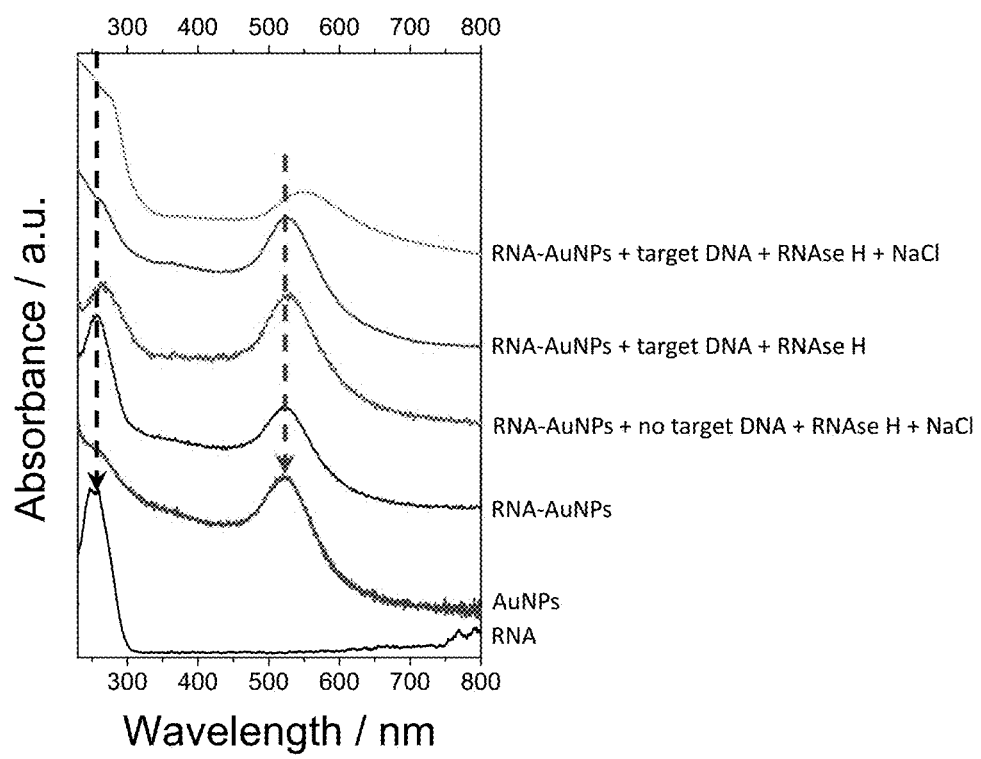
FIG. 9 depicts the functionalisation of AuNPs with RNA. The graph demonstrates the wavelength spectrum (230-800 nm) of bare-AuNP (d=17±3 nm, red curve) with a maximum absorbance peak at 520 nm (red arrow), and RNA in buffer alone demonstrating a peak absorbance at 260 nm (black curve, black arrow), and the RNA-AuNP conjugates (blue curve). This result was used to confirm successful functionalisation of RNA onto the AuNP surface as demonstrated by an absorbance peak at 525 nm (LSPR) and 260 nm (RNA) post centrifuging to remove unbound RNA. Control experiments were carried out to provide further illustration that RNA is cleaved by RNAse H enzyme and subsequent addition of NaCl induces aggregation. The assay was conducted as stated in methods section, subsection Colorimetric detection of pathogenic bacterial DNA prior to NaCl addition. Post incubation with the endonuclease enzyme, the samples containing 0 and 10 µM target DNA was centrifuged at 13,000 g for 10 minutes, decanted and suspended in 45 µL of ultrapure $H_2O$. UV-Vis measurements were carried out (230-800 nm) prior to the addition of NaCl (final effective concentration of 2 M) and compared to the full wavelength spectrum post addition. The results show a diminished peak at 260 nm (olive curve), and a broadened plasmonic peak at 556 nm when the 2 M NaCl is added (orange curve). This suggests that the enzyme has cleaved the RNA from the surface of the AuNP, resulting in the unprotected AuNPs. In contrast, the RNA absorbance peak 260 nm still persists, and no broadened plasmonic peak is observed for the zero DNA sample (magenta curve).

Gold nanoparticles (AuNPs) (17±3 nm, FIG. 8) were first synthesized by a method reported previously with minor alterations[2] and exhibited a typical UV-vis absorbance band at 520 nm. Subsequently, a single-stranded RNA probe (5'-Amino-C6-AGG UGU GGA CGA CGU CAA GUC AUC AUG-3') was designed to recognize a DNA fragment of *Campylobacter jejuni*, (NCTC 11168=ATCC 700819 chromosome, 5'-CAT GAT GAC TTG ACG TCG TCC ACA CCT-3'). The RNA probe was successfully crafted onto the AuNP via an N-hydroxysuccimidyl (NHS) ester of thioctic acid. The AuNP-RNA conjugate exhibits a deep red colour, and absorbance peaks at 525 nm and 260 nm (FIG. 9), which represents the typical optical absorption of AuNPs and RNA, respectively. The shift in LSPR peak from 520 nm (bare nanoparticles), to 525 nm with the AuNP-RNA conjugates further demonstrates the successful functionalisation. The RNA-functionalized AuNPs prepared by this method show excellent stability under high electrolytic conditions (zero to 2 M NaCl) (FIG. 7). In the presence of target *Campylobacter jejuni* DNA, hybridization occurs with RNA functionalized onto the AuNP surface. The subsequent DNA-RNA heteroduplex becomes a target for cleavage of the RNA probe via RNase H enzyme, allowing the DNA to liberate and hybridize with another RNA strand (FIG. 1, overall scheme). This happens isothermally and iteratively until all of the RNA probes are cleaved, leaving the nanoparticles denuded. The addition of 2 M NaCl causes the denuded nanoparticles to aggregate in solution, initiating a colour change from red to blue. The aggregation state was confirmed in FIG. 2 by the transmission electron microscopy (TEM) analysis of RNA-functionalized AuNPs under assay conditions in the absence and presence (1 µM) of target DNA. The distinct colour change generated from the assay can be detected by the unaided eye, or by simple spectroscopic analysis.

Figure 3:
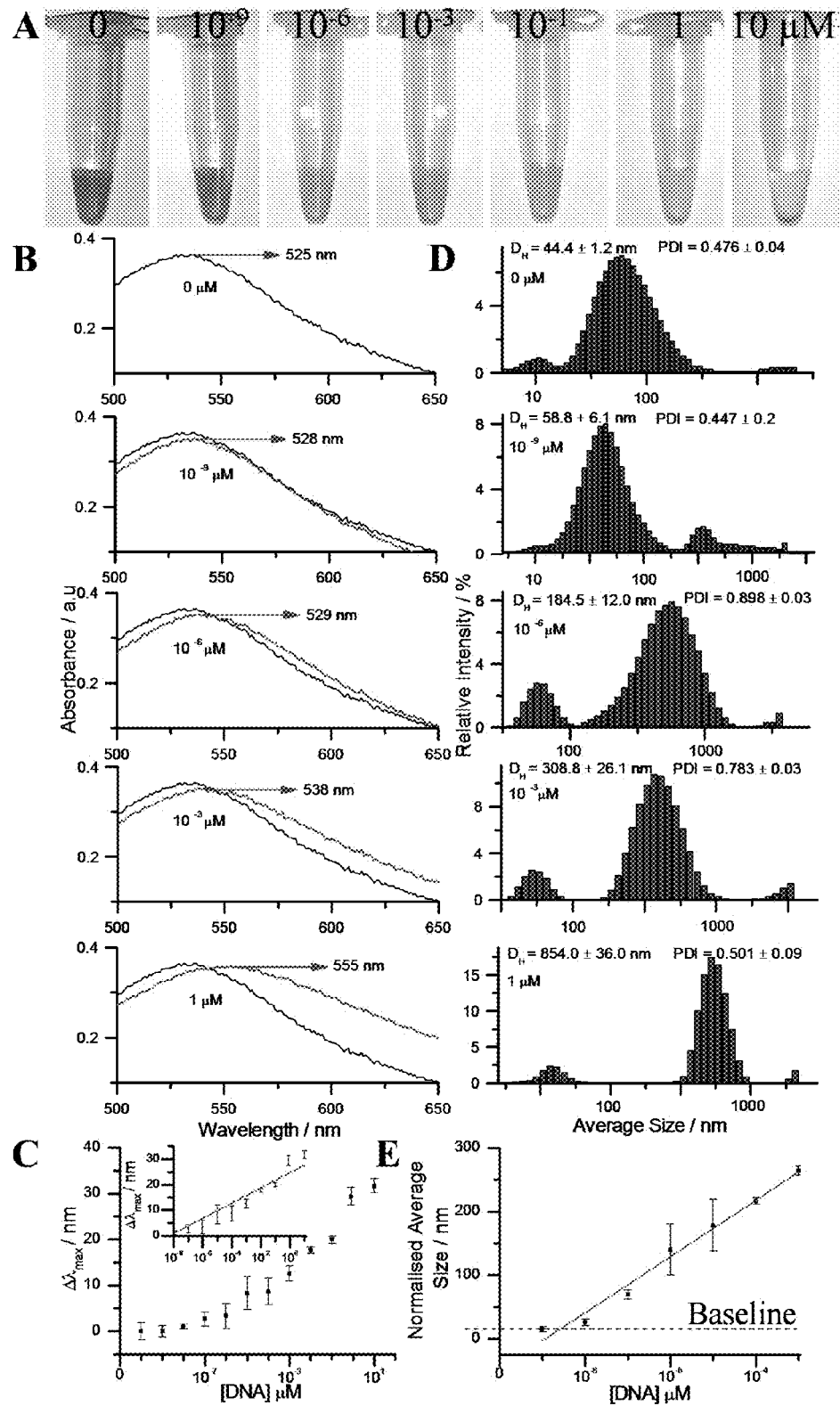
FIG. 3 depicts the results of analysis of AuNP-RNA conjugates in the presence of increasing concentrations of target DNA. (A) A representative colour photograph showing a visual colour change from red to blue or transparent with increasing DNA concentrations. (B) UV-vis absorption spectra demonstrating a red shift towards longer wavelengths (525 nm to 555 nm) in the presence of increasing target DNA concentrations. (C) Wavelength shift of the LSPR peak as a function of target DNA concentration (n=3). Inset: the linear relationship between target DNA concentration and maximum wavelength shift ($R^2$=0.93). (D) Hydrodynamic size distribution of AuNPs measured by dynamic light scattering (DLS) technique. (E) Linear relationship between target DNA concentration and average increase in AuNP size derived from DLS analysis ($R^2$=0.98).

To test the hypothesis of the assay, a 10-fold dilution of target DNA ranging from 0 to 10 µM concentration was analyzed. FIG. 3A demonstrates the visible colour change of AuNP-RNA solution from red to blue or grey, with increasing target DNA concentration. The lowest target DNA concentration easily determined by the naked eye was $10^{-6}$ µM, as seen by a colour change from red to light blue, caused by a decrease in interparticle distance. More quantitatively, UV-vis absorption measurements were performed to determine the LSPR shift as a function of target DNA concentration (FIG. 3B). The results demonstrate a shift in wavelength from a target DNA concentration of 10 fM, which continues to increase to 10 µM (FIG. 3C). A good linear relationship between the LSPR shift and target DNA concentration (FIG. 3C, inset) could be obtained for a range between 10 fM and 10 µM of target DNA ($R^2$=0.93). The limit of detection (LOD) is defined as the lowest DNA concentration with a response three times greater than the standard deviation (SD) of the blank sample. Owing to the excellent stability of the AuNP-RNA conjugate, the SD value of the zero concentration for ten measurements (n=10) was as small as 1.9 nm, thus the LOD of the current assay is 40.7 fM of pathogenic bacterial DNA. The LOD is about two orders of magnitude more sensitive in comparison to a similar method utilizing fluorescein[1] and other AuNP-functionalized based assays for the detection of DNA.[1,3,4]

During the UV-vis analysis, we observed that the aggregated AuNPs had latched on to the wall of the Eppendorf tube or settled down to the bottom of the tube, potentially causing only free and partially aggregated particles to be measured in solution. Thus, it is evident that the LSPR shift is not as predominant when compared to the colorimetric response as seen in the colour photographs (FIG. 3B). Therefore, to accurately reflect the aggregation states of the AuNPs, dynamic light scattering (DLS) measurements were carried out to determine the average size of the AuNP-conjugates in the presence varying target DNA concentrations. DLS data is displayed as the integrated value of three measurements derived from one sample. The polydispersity index (PDI) for each sample is also displayed which indicates the variation of nanoparticle size within a distribution. The PDI is calculated from the distribution width and mean, giving an overall indication of the non-uniformity of particles within a sample. The DLS results show an average increase in AuNP size, from 44.4 nm (±1.2 nm) with the zero concentration sample to 854.0 nm (±36.0 nm) at 1 µM target DNA concentration, which demonstrates increased aggregation with increasing target DNA concentration (FIG. 3D). Furthermore, the size distribution charts show a shift in average size from one population, between 10-100 nm to a second, increasing population (100 to 1000 nm). This large size distribution can be explained by the highly sensitive nature of DLS analysis which is capable of determining the true state of particles in a given media, compared to TEM which only measures the solid state (nanoparticles are dried on grid subsequent to analysis). Furthermore, DLS measures the hydrodynamic diameter of the particle, which in this case includes the metallic core and RNA functionalised onto the surface, thus it is obvious that one should see this wide distribution. The PDI data demonstrates broad polydispersion which increases from 0 µM to $10^{-3}$ µM target DNA concentration, where the index value decreases. This indicates a wide size distribution at lower target DNA concentrations, with narrower size distributions at higher concentrations. This coincides with the distribution data which indicates that there are a greater number of larger or aggregated particles at a high target DNA concentration, in contrast with lower target DNA concentrations which demonstrate a larger size frequency over several distribution sizes (i.e. 10-100 nm and 100-1000 nm). FIG. 3E demonstrates the linear fitting of AuNP size increase as a function of target DNA concentration ($R^2$=0.98). This data provides a dynamic range of between 1 fM and 100 pM of target DNA. From these we can determine a LOD of 2.45 fM of target DNA as there is some degree of AuNP aggregation, which is not visible to the naked-eye or detectable using UV-vis spectrophotometry. A baseline has been included in FIG. 3E to remove background signal as determined by specificity and selectivity analysis.

Figure 4:
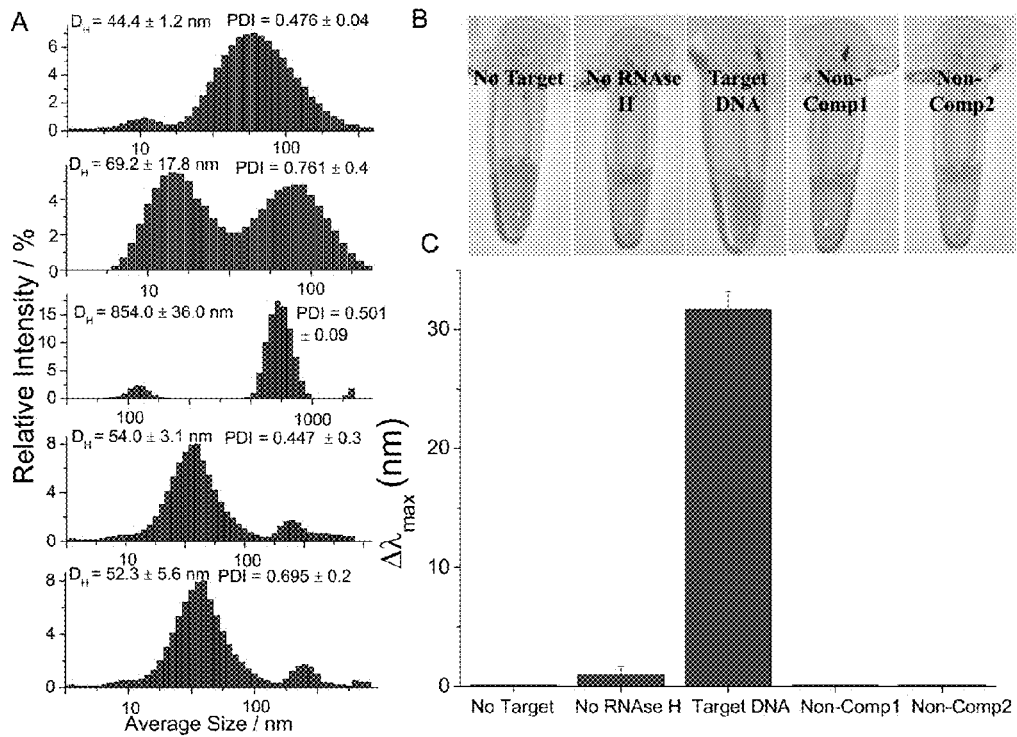
FIG. 4 depicts the results of experiments demonstrating assay specificity. (A) DLS measurements demonstrating the hydrodynamic size distribution of AuNP-RNA post assay conditions. From top to bottom: RNAse H enzyme and 0 μM target DNA; no RNAse H enzyme and 10 μM target DNA; RNAse H enzyme and 1 μM target DNA; RNAse H enzyme and 10 μM non-complementary DNA sequence 1; and RNAse H enzyme and 10 μM non-complementary DNA sequence 2. (B) and (C) are the corresponding colour photograph and maximum wavelength shift of LSPR peak under different conditions (n=3), respectively.

Control experiments were carried out with RNAse H enzyme removed to determine if nanoparticle aggregation was fully attributed to the enzymatic cleavage of RNA (target DNA concentration was fixed at 10 μM). In the absence of target DNA but in the presence of RNAse H enzyme, the average AuNP size was determined to be 44.4±1.2 nm (FIG. 4A) with no visible change in colorimetric response (FIG. 4B) and no shift in LSPR peak (maximum absorbance peak at 525 nm; FIG. 4C). In the absence of RNAse H but in the presence of 10 μM target DNA, the hybridization of the RNA-DNA resulted in an increase in the average size of the nucleotide-AuNP complex of 24.8 nm as compared to the zero (no target) sample (FIG. 4A). The UV-vis results further demonstrate that the removal of RNAse H enzyme results in almost no change in the LSPR peak shift. This result confirms that the addition of RNAse H enzyme is essential in controlling aggregation of the AuNPs through cleavage of functionalised RNA.

Control experiments were also carried out with two non-complementary DNA sequences at a concentration of 10 μM. The DLS results demonstrate a slight increase in particle complex size with a maximum value of 9.6 nm (FIG. 4A), attributing to the background noise of the assay (also denoted as the baseline on FIG. 3E). The colour images in FIG. 4B along with the UV-vis results (FIG. 4C) demonstrate no visual or spectroscopic change in colour or LSPR peak under the test experiments. The high specificity of the assay can be credited to the specific DNA-RNA recognition and hybridisation, as well as subsequent highly selective RNAse H enzyme cleavage of the RNA in the heteroduplex.

Figure 5:
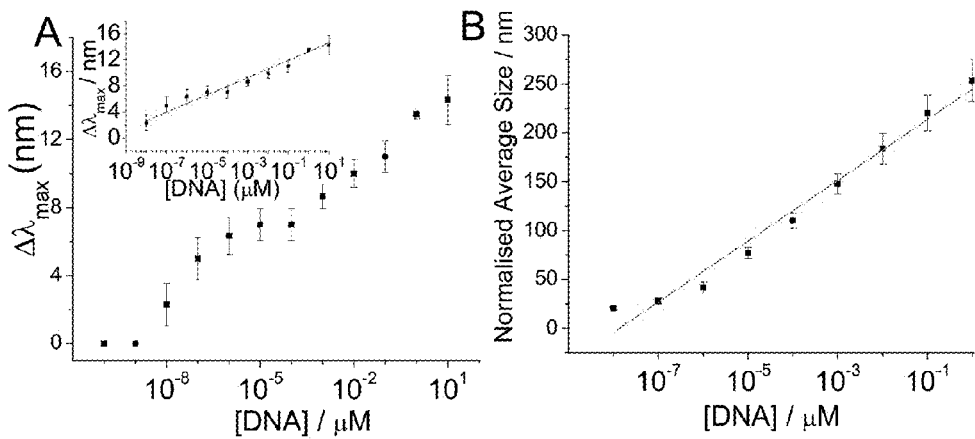
FIG. 5 depicts (A) the wavelength shift of the LSPR peak as a function of target DNA concentration analyzed in chicken matrix, demonstrating the sensitivity of the assay. Inset is the linear relationship between target DNA concentration spiked in chicken matrix and maximum wavelength shift ($R^2$=0.96), and (B) the linear relationship between target DNA prepared in chicken matrix and normalized, average increase in nanoparticle size determined by dynamic light scattering technique (DLS) ($R^2$=0.98).
Figure 6:
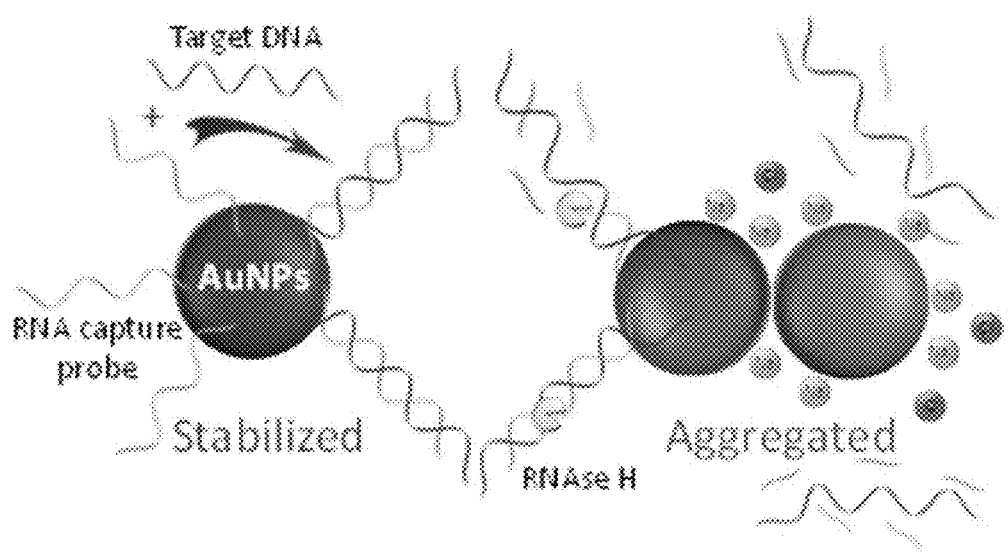
FIG. 6 depicts how RNAse H enzyme and gold nanoparticles (AuNPs) are successfully utilized in the development of a biological sensor for the detection of nucleic acids at a highly sensitive limit of detection of 2.45 fM. AuNPs are functionalized with a specific RNA probe. In the presence of target DNA, RNAse H enzyme catalyses the cleavage of RNA within and RNA-DNA heteroduplex structure, leading to gold nanoparticle aggregation upon addition of NaCl.

The applicability of the assay was tested by preparing a 10-fold dilution of target DNA ranging from 0 to 10 μM in chicken matrix. FIG. 5A shows the maximum LSPR shift, as a function of target DNA in chicken matrix. The results demonstrate good linearity ($R^2$=0.96) spanning from 10 fM and 10 μM. In the complex environment, the spiked target DNA was identified at concentration as low as 1.2 pM based on the LSPR analysis. It was noted that the LOD had increased two orders of magnitude in comparison to buffer conditions and there was an overall decrease in maximum LSPR shift (15 nm), which might be attributable to interferences of the enzymatic reaction within the sample. Furthermore, parallel DLS measurements were carried out to determine the aggregation states of AuNPs post analysis in chicken matrix. FIG. 5B demonstrates the linear correlation between normalized average size (nm) and DNA concentration (μM). The linear range of the assay was determined to be between 10 fM and 1 μM, with a lowest detectable limit of around 100 fM. Thus, the assay shows good application to food analysis.

CONCLUSION

In conclusion, we have presented a highly sensitive and selective method for the detection of DNA, based on endonuclease controlled aggregation of plasmonic AuNPs. RNAse H enzymatic cleavage in combination with DNA-RNA hybridization provides a highly specific and ultra-sensitive assay, which can detect 1 pM target DNA concentration visibly or down to femtomolar level by spectroscopic techniques (40.7 and 2.45 fM as measured by UV-vis and dynamic light scattering (DLS), respectively). The detection capabilities within a food matrix show good sensitivity (1.2 pM and 18 fM as analyzed by UV-vis and DLS, respectively). In addition to the ultra-high sensitivity, the total analysis time of the assay is less than 3 hours, thus demonstrating its practicality for food analysis. The versatility of probe design and enzyme cleavage offers a broad range of potential applications for the detection of DNA. Future work will focus on further applications of the method and potential multiplexing capabilities for real clinical and veterinary samples.

REFERENCES

[1] J. Kim, R. Estabrook, G. Braun, B. Lee, N. Reich, Chem. Commun. (Camb), 2007, 42, 4342-4344;
[2] J. Turkevich, P. C. Stevenson, J. Hillier, Discuss. Faraday Soc. 1951, 11, 55-75;
[3] L. Cui, G. Ke, W. Y. Zhang, C. J. Yang, Biosensors and Bioelectronics, 2011, 5, 2796-2800;
[4] Q. Fan, J. Zhao, H. Li, L. Zhu, G. Li, Biosensors and Bioelectronics, 2012, 1, 211-215.

The invention is not limited to the embodiments described herein but can be amended or modified without departing from the scope of the present invention.

The invention claimed is:

1. A method for detecting a target deoxyribonucleic acid (DNA) in a sample, the method comprising: a) contacting the sample with a plurality of metal nanoparticles functionalized with one or more ribonucleic acid (RNA) probes; b) forming a heteroduplex between the target DNA and RNA probe on an RNA-functionalized metal nanoparticle; c) contacting the heteroduplex of target DNA and RNA probe on the RNA-functionalized metal nanoparticle with an enzyme that cleaves RNA in a DNA-RNA heteroduplex thereby releasing the target DNA; d) repeating steps (b) and (c) until all, or substantially all, of the RNA probes on the plurality of RNA-functionalized metal nanoparticles have been cleaved from the metal nanoparticles; and e) aggregating the metal nanoparticles from which all, or substantially all, of the RNA probes have been cleaved, wherein the aggregating is performed in the presence of a salt in a final concentration of from about 1M to 10M, thereby indicating the presence of the target DNA, and wherein limit of the detection of said method is about ≤1 pM.

2. The method of claim 1, wherein the metal nanoparticles comprise noble metal nanoparticles.

3. The method of claim 2, wherein the metal nanoparticles are gold nanoparticles.

4. The method of claim 1, wherein the metal nanoparticles are functionalised with one or more RNA probes by conjugating the one or more RNA probes to each metal nanoparticle via a modification at the 5' end or the 3' end of each RNA probe.

5. The method of claim 4, wherein the modification is an amine modification, a sulfide modification, a disulphide modification, a thiol modification, or a dithiol modification.

6. The method of claim 5, wherein the dithiol modification is a thioctic acid modification.

7. The method of claim 1, wherein the sample contains double-stranded DNA and the sample is treated, prior to or at the same time as step (a), such that at least some of the double-stranded DNA dissociates to single-stranded DNA.

8. The method of claim 1, wherein, in step (b), the heteroduplex comprising the target DNA and the RNA probe on the RNA-functionalised metal nanoparticle is formed by maintaining the sample at a temperature of about 40° C. to about 70° C., optionally for about 0.5 hours to about 2 hours.

9. The method of claim 1, wherein the enzyme is an enzyme that cleaves phosphodiester bonds in the RNA probe in the heteroduplex.

10. The method of claim 9, wherein the enzyme is a ribonuclease enzyme, optionally wherein the enzyme is RNase H.

11. The method of claim 1, wherein at least steps (c) and (d) are carried out under substantially isothermal conditions.

12. The method of claim 1, wherein the salt is sodium chloride (NaCl), potassium chloride (KCl), calcium chloride ($CaCl_2$), magnesium chloride ($MgCl_2$), Manganese chloride ($MnCl_2$), or a mixture thereof.

13. The method of claim 1, wherein the aggregation of the metal nanoparticles causes the metal nanoparticles to change colour thereby indicating the presence of the target DNA.

14. The method of claim 13, wherein the metal nanoparticles are gold nanoparticles and the aggregation of the gold nanoparticles causes the light emission wavelength of the gold particles to shift from about 525 nm to a wavelength of greater than about 525 nm thereby indicating the presence of the target DNA.

15. The method of claim 13, wherein the change of colour of the nanoparticles is detected by the naked eye, spectrophotometrically, transmission electron microscopy or a dynamic light scattering technique.

16. A kit for detecting a target DNA in a sample, wherein the kit is used according to the method of claim 1.

17. The kit of claim 16, wherein the kit comprises a plurality of metal nanoparticles and one or more RNA probes for functionalising the metal nanoparticles and which are suitable for the detection of the target DNA, wherein optionally the kit further comprises an enzyme that cleaves phosphodiester bonds in the RNA probe in a DNA-RNA heteroduplex.

18. The kit of claim 16, wherein the kit comprises gold nanoparticles functionalised with one or more RNA probes suitable for the detection of the target DNA, wherein optionally the kit further comprises an enzyme that cleaves phosphodiester bonds in the RNA probe in a DNA-RNA heteroduplex.

19. The method of claim 1, wherein the limit of detection of the method is about ≤1 pM as determined by the naked eye.

20. The method of claim 1, wherein the limit of detection of the method is about ≤40.7 fM as measured by UV-visible light spectrophotometry.

21. The method of claim 1, wherein the limit of detection of the method is about ≤2.45 fM as measured by dynamic light scattering (DLS).

\* \* \* \* \*